(12) United States Patent
Lai et al.

(10) Patent No.: US 7,198,639 B2
(45) Date of Patent: Apr. 3, 2007

(54) POLYSILSESQUIOXANE CONTAINING POLYMERIC COMPOSITIONS

(75) Inventors: Yu-Chin Lai, Pittsford, NY (US); James A. Bonafini, Jr., Pittsford, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 10/243,564

(22) Filed: Sep. 13, 2002

(65) Prior Publication Data

US 2004/0054047 A1 Mar. 18, 2004

(51) Int. Cl.
*H61F 2/16* (2006.01)

(52) U.S. Cl. ............ 623/6.11; 525/477; 525/478; 528/25; 528/26; 528/28; 528/31; 528/32

(58) Field of Classification Search ........ 526/279; 351/159; 525/474, 476, 477, 478, 479; 264/1.1, 264/145; 556/450, 460; 528/25, 26, 27, 528/28, 29, 33, 37; 623/6.56, 6.11; 604/294
See application file for complete search history.

(56) References Cited

U.S. PATENT DOCUMENTS

| | | | | |
|---|---|---|---|---|
| 3,996,187 A | | 12/1976 | Travnicek | 260/37 |
| 3,996,189 A | | 12/1976 | Travnicek | 260/37 |
| 4,304,895 A | * | 12/1981 | Loshaek | 526/313 |
| 4,418,165 A | | 11/1983 | Polmanteer et al. | 523/210 |
| 4,647,282 A | | 3/1987 | Fedorov et al. | 623/4 |
| 4,868,251 A | | 9/1989 | Reich et al. | 525/479 |
| 5,047,492 A | * | 9/1991 | Weidner et al. | 528/15 |
| 5,444,106 A | * | 8/1995 | Zhou et al. | 523/107 |
| 5,466,768 A | | 11/1995 | Yang | 528/15 |
| 5,484,867 A | * | 1/1996 | Lichtenhan et al. | 528/9 |
| 5,512,609 A | | 4/1996 | Yang | 523/107 |
| 5,623,029 A | | 4/1997 | Yang | 525/478 |
| 5,723,541 A | * | 3/1998 | Ingenito et al. | 525/464 |
| 6,100,417 A | * | 8/2000 | Lichtenhan et al. | 556/460 |
| 6,252,030 B1 | * | 6/2001 | Zank et al. | 528/31 |
| 6,425,936 B1 | * | 7/2002 | Sammons et al. | 95/45 |
| 6,432,137 B1 | | 8/2002 | Nanushyan et al. | 623/6.11 |
| 6,569,932 B2 | * | 5/2003 | Hsiao et al. | 524/269 |
| 6,623,711 B2 | | 9/2003 | Lyu et al. | |
| 6,933,345 B1 | * | 8/2005 | Lichtenhan et al. | 525/101 |
| 2002/0198282 A1 | * | 12/2002 | Jia | 523/115 |
| 2003/0050408 A1 | * | 3/2003 | Puhala et al. | 525/479 |
| 2003/0055193 A1 | * | 3/2003 | Lichtenhan et al. | 528/10 |
| 2003/0120099 A1 | * | 6/2003 | Laine et al. | 556/450 |

FOREIGN PATENT DOCUMENTS

WO WO 01/46295 A1 6/2001
WO WO 02/50144 A2 * 6/2002

OTHER PUBLICATIONS

Li et al. "Polyhedral Oligomeric Silsesquioxane (POSS) Polymers and Copolymers: A Review", Journal of Inorganic and Organometallic Polymers, vol. 11, No. 3, pp. 123-154, Sep. 2001.*

* cited by examiner

Primary Examiner—Marc S. Zimmer

(57) ABSTRACT

Soft, durable, polymeric compositions with one or more reactive polyhedral oligomeric silsesquioxane reinforcing agents and ophthalmic devices such as for example intraocular lenses and corneal inlays made therefrom are described herein.

29 Claims, No Drawings

POLYSILSESQUIOXANE CONTAINING POLYMERIC COMPOSITIONS

FIELD OF THE INVENTION

The present invention relates to polymeric compositions useful in the manufacture of biocompatible medical devices. More particularly, the present invention relates to the use of reactive polyhedral oligomeric silsesquioxanes with definite structures as reinforcing agents for silicone compositions having desirable physical characteristics and refractive indices for use in the manufacture of ophthalmic implants.

BACKGROUND OF THE INVENTION

Since the 1940's optical devices in the form of intraocular lens (IOL) implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. In general, the materials of current commercial IOLs fall into one of three categories: silicones, hydrophilic acrylics and hydrophobic acrylics.

In general, high water content hydrophilic acrylics, or "hydrogels," have relatively low refractive indices, making them less desirable than other materials with respect to minimal incision size. Low refractive index materials require a thicker IOL optic portion to achieve a given refractive power. Silicone elastomers are usually fabricated from the hydrosilation of a vinyl-containing polysiloxane and a hydrosilane-containing polysiloxane. Elastomers so produced are rather weak mechanically, unless a reinforcing agent, typically a silica, is included in the formulation. Silicone elastomers that include such a reinforcing agent are currently used and commercially available through such products as the SILSOFT™ contact lens (Bausch & Lomb Incorporated, Rochester, N.Y.) and the CHIROFLEX™ intraocular lens (Bausch & Lomb Incorporated, Rochester, N.Y.). Low glass transition temperature hydrophobic acrylic materials are desirable because they typically have a high refractive index and unfold more slowly and more controllably than silicone materials. Unfortunately, low glass transition temperature hydrophobic acrylic materials, which contain little or no water initially, may absorb pockets of water in vivo causing light reflections or "glistenings." Furthermore, it may be difficult to achieve ideal folding and unfolding characteristics due to the temperature sensitivity of some acrylic polymers.

Because of the noted shortcomings or difficulties associated with current polymeric materials available for use in the manufacture of ophthalmic devices, there is a need for stable, biocompatible polymeric materials having desirable physical characteristics and refractive indices.

SUMMARY OF THE INVENTION

Soft, foldable, high elongation, polymeric compositions of the present invention are synthesized through hydrosilation, epoxy reaction, urethane/urea formation, free radical copolymerization or other types of reactions. Production processes of the present invention using reactive polyhedral oligomeric silsesquioxanes (POSS) with definite structures as reinforcing agents, produce polymeric compositions having desirable physical properties for use in the manufacture of ophthalmic devices. The polymeric compositions of the present invention are transparent and have relatively high strength for durability during surgical manipulation, relatively high elongation and relatively high refractive index. The subject polymeric compositions are particularly well suited for use in the manufacture of ophthalmic devices such as intraocular lens (IOL) implants, keratoprostheses, corneal rings, corneal inlays and the like.

Preferred reactive polyhedral oligomeric silsesquioxanes for use as a reinforcing agent in the production of the polymeric compositions of present invention have a structure generally represented by Formula 1 below:

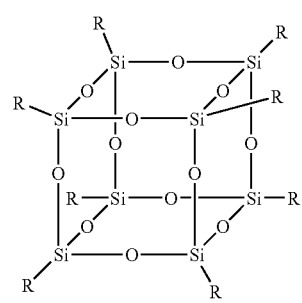

Formula 1 wherein the R groups may be the same or different with at least one of the R groups being a reactive group, R reactive groups may be the same or different selected from the group consisting of hydrogen, hydroxy, alkoxy, amine, chlorine, epoxide, isocyanate, methacrylate, acrylate, methacrylamide, acrylamide, nitrile, norbornenyl, vinyl, styrenyl and thiol; R nonreactive groups may be the same or different selected from the group consisting of $C_{1-30}$ alkyl and $C_{6-30}$ aryl.

As illustrated by the structure of Formula 1, all eight silicone atoms together form a cubic cage or a "T8" structure. T8 is used to describe the subject structure wherein the "T" refers to three oxygen atoms connecting to each silicon atom and "8" refers to eight silicon atoms forming a cage. If one silicon atom is removed from the T8 structure to leave an "open position", the open position of the remaining T7 structure is replaced with an R group as defined above.

Accordingly, it is an object of the present invention to provide transparent, biocompatible polymeric compositions having desirable physical characteristics and relatively high refractive indices.

Another object of the present invention is to provide polymeric compositions having relatively high elasticity and good clarity.

Another object of the present invention is to provide polymeric compositions suitable for use in the manufacture of ophthalmic devices.

Another object of the present invention is to provide polymeric compositions suitable for use in the manufacture of intraocular lens implants.

Still another object of the present invention is to provide polymeric compositions that are economical to produce.

These and other objectives and advantages of the present invention, some of which are specifically described and others that are not, will become apparent from the detailed description and claims that follow.

DETAILED DESCRIPTION OF THE INVENTION

Silicone elastomers are usually fabricated from the hydrosilation of a vinyl-containing polysiloxane and a hydrosilane-containing polysiloxane. Elastomers so produced are rather weak mechanically, unless a reinforcing agent, typically a silica, is included in the formulation. Accordingly, the present invention relates to the use of reactive polyhedral oligomeric silsesquioxanes (POSS) with definite structures as reinforcing agents for silicone elastomers. Each POSS molecule has at least one reactive group. The POSS of the present invention are useful as reinforcing agents in polymeric compositions suitable for use in the manufacture of ophthalmic devices such as but not limited to intraocular lenses, corneal inlays and corneal rings. The preferred reactive POSS molecules of the present invention are represented generally by Formula 1 below:

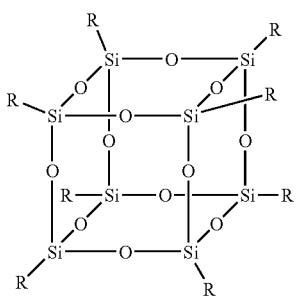

Formula 1 wherein the R groups may be the same or different with at least one of the R groups being a reactive group, R reactive groups may be the same or different selected from the group consisting of hydrogen, hydroxy, alkoxy, amine, chlorine, epoxide, isocyanate, methacrylate, acrylate, methacrylamide, acrylamide, nitrile, norbornenyl, vinyl, styrenyl and thiol; R nonreactive groups may be the same or different selected from the group consisting of $C_{1-30}$ alkyl and $C_{6-30}$ aryl.

The subject POSSes with definite structures are reliably reproducible, which differs significantly from the indefinite structures of silicone resin. Examples of suitable POSSes with definite structures of the present invention include but are not limited to the following molecules, most of which are T8 structures with one to eight reactive sites or T7 structures with three reactive sites.

OH-Containing: An OH-containing POSS for example, but not to be limited thereto, is octahydroxypropyidimethylsilyl-POSS.

Alkoxy-Containing: Alkoxy-containing POSSes include for example but are not limited to diethoxymethylsilylethyl-cyclohexyl-POSS, diethoxymethylsilylethyl-isobutyl-POSS, diethoxymethylsilylpropyl-cyclohexyl-POSS, diethoxymethylsilylpropyl-isobutyl-POSS, ethoxydimethyl-silylethyl-cyclohexyl-POSS, ethoxydimethylsilylethyl-isobutyl-POSS, ethoxydimethylsilylpropyl-cyclohexyl-POSS, ethoxydimethylsilylpropyl-isobutyl-POSS, diethoxymethylsilylethyl-cyclohexyl-POSS, triethoxysilyl-ethyl-isobutyl-POSS, triethoxysilylpropyl-cyclohexyl-POSS and triethoxylsilylpropyl-isobutyl-POSS, with ethoxydimethylsilylethyl-isobutyl-POSS and ethoxydimethylsilylpropyl-isobutyl-POSS as the preferred.

Amine-Containing: Amine-containing POSSes include for example but are not limited to aminopropyl cyclohexyl-POSS, aminopropyl isobutyl-POSS, aminopropyl isooctyl-POSS and octaaminophenyl POSS, with aminopropyl isobutyl-POSS as the preferred.

Chlorosilane-Containing: Chlorosilane-containing POSSes include for example but are not limited to monochlorocyclohexyl-POSS, monochlorocyclopentyl-POSS, monochloroisobutyl-POSS, chlorodimethylsilylethyl isobutyl-POSS, chlorodimethylsilylpropyl isobutyl-POSS, chlorodimethylsilylpropyl cyclohexyl-POSS, dichloromethylsilylethyl isobutyl-POSS, dichloromethylsilylpropyl isobutyl-POSS, dichloromethylsilylpropyl cyclohexyl-POSS, trichlorosilylethyl isobutyl-POSS, trichlorosilyipropyl isobutyl-POSS, trichlorosilylpropyl cyclohexyl-POSS and octa(chlorodimethysilylethyl)-POSS with chlorodimethylsilylpropyl isobutyl-POSS as the preferred.

Epoxide-Containing: Epoxide-containing POSSes include for example but are not limited to epoxypropyl isobutyl-POSS, epoxypropyl cyclopentyl-POSS, glycidyl cyclohexyl-POSS, glycidyl isobutyl-POSS, glycidyl isooctyl-POSS, glycidyl phenyl-POSS, octaepoxycyclohexyldimethylsilyl-POSS, octaglycidyldimethylsilyl-POSS, triglycidyl cyclohexyl-POSS, triglycidyl cyclopentyl-POSS, triglycidyl isobutyl-POSS and triglycidyl ethyl-POSS, with epoxypropyl isobutyl-POSS, glycidyl isobutyl-POSS, and triglycidyl isobutyl-POSS as preferred.

Isocyanate-Containing: Isocyanate-containing POSSes include for example but are not limited to isocyanatopropyldimethylsiloxy cyclohexyl-POSS and isocyanatopropyldimethylsiloxy isobutyl-POSS with isocyanatopropyldimethylsiloxy isobutyl-POSS as the preferred.

Acrylate/Methacrylate-Containing: Acrylate/methacrylate-containing POSSes include for example but are not limited to acryloxypropyl cyclohexyl-POSS, acryloxypropyl cyclopentyl-POSS, acryloxypropyl isobutyl-POSS, methacryloxypropyl cyclohexyl-POSS, methacryloxypropyl cyclopentyl-POSS, methacryloxypropyl isobutyl-POSS, methacryloxypropyl ethyl-POSS, methacryloxypropyl isooctyl-POSS, methacryloxypropyl phenyl-POSS, octamethacryloxypropyl-POSS, methacryloxypropyldimethylsilyl cyclopentyl-POSS and methacryloxypropyl-dimethylsilyl cyclopentyl-POSS with acryloxypropyl isobutyl-POSS, methacryloxypropyl isobutyl-POSS and methacryloxypropyl-dimethylsilyl cyclopentyl-POSS as the preferred.

Acrylamide/Methacrylamide-Containing: Acrylamide/methacrylamide-containing POSSes include for example but are not limited to acrylamidopropyl cyclohexyl-POSS, acrylamidopropyl cyclopentyl-POSS, acrylamidopropyl cyclohexyl-POSS, methacrylamidopropyl cyclohexyl-POSS, methacrylamidopropyl cyclopentyl-POSS, methacrylamidopropyl cyclohexyl-POSS, with acrylamidopropyl cyclohexyl-POSS as the preferred.

Nitrile-Containing: Nitrile-containing POSSes include for example but are not limited to cyanopropyl cyclohexyl-POSS, cyanopropyl cyclopentyl-POSS, cyanopropyl isobutyl-POSS, cyanoethyl cyclohexyl-POSS, cyanoethyl cyclopentyl-POSS and cyanoethyl isobutyl-POSS with cyanopropyl isobutyl-POSS and cyanoethyl isobutyl-POSS as preferred.

Norbornenyl-containing: Norbornenyl-containing POSSes include for example but are not limited to norbornenylethyl cyclohexyl-POSS, norbornenylethyl cyclopentyl-POSS, norbornenylethyl isobutyl-POSS, trisnorbornenylethyldimethylsilyl cyclopentyl-POSS, trisnorbornenylethyldimethylsilyl cyclohexyl-POSS and trisnorbornenylethyldimethylsilyl isobutyl-POSS with norbornenylethyl isobutyl-POSS and trisnorbornenylethyldimethylsilyl isobutyl-POSS as the preferred.

Vinyl-Containing: Vinyl-containing POSSes include for example but are not limited to allyl cyclohexyl-POSS, allyl cyclopentyl-POSS, allyl butyl-POSS, allyidimethylsilylcyclopentyl-POSS, cyclohexenylethyl cyclopentyl-POSS, vinyldimethylsilyl cyclopentyl-POSS, vinyldiphenylsilyl cyclopentyl-POSS, vinyl cyclopentyl-POSS, vinyl cyclohexyl-POSS, vinyl isobutyl-POSS, tris-vinyldimethyl cyclohexyl-POSS, tris-vinyidimethyl cyclopentyl-POSS, tris-vinyidimethyl isobutyl-POSS and octavinyldimethyl-POSS with allyl butyl-POSS, vinyl isobutyl-POSS and octavinyldimethylsilyl-POSS as preferred.

Hydrogen-Containing: Hydrogen-containing POSSes include for example but are not limited to dimethyihydrosilyl cyclohexyl-POSS, dimethylhydrosilyl cyclopentyl-POSS, dimethylhydrosilyl isobutyl-POSS, monohydro cyclohexyl-POSS, monohydro isobutyl-POSS, octadimethylhydrosilyl-POSS, trisdimethylhydrosilyl cyclohexyl-POSS and trisdimethylhydrosilyl isobutyl-POSS with dimethylhydrosilyl isobutyl-POSS, monohydro isobutyl-POSS and trisdimethylhydrosilyl isobutyl-POSS as the preferred.

Thiol-Containing: Thiol-containing POSSes include for example but are not limited to mercaptopropyl cyclohexyl-POSS, mercaptopropyl cyclopentyl-POSS and mercaptopropyl isobutyl-POSS.

Silanol-Containing: Silanol-containing POSSes include for example but are not limited to monohydroxy cyclohexyl-POSS, monohydroxy cyclopentyl-POSS, monohydroxy isobutyl-POSS, trishydroxy cyclohexyl-POSS, trishydroxy cyclopentyl-POSS, trishydroxy isobutyl-POSS, trishydroxy isooctyl-POSS, trishydroxy ethyl-POSS and trishydroxy phenyl-POSS with monohydroxy isobutyl-POSS, trishydroxy isobutyl-POSS and trishydroxy isooctyl-POSS as the preferred.

Styrene-Containing: Styrene-containing POSSes include for example but are not limited to p-Styryl cyclohexyl-POSS, p-styryl cyclopentyl-POSS and p-styryl isobutyl-POSS.

Some reactive POSSes having multiple reactive sites have different reactive groups that are not reactive toward each other. Such POSSes are also useful as reinforcing agents in accordance with the present invention. Some examples of such POSSes are norbornenylethyldimethylsilyldihydroxy isobutyl-POSS and methacryloxypropylsilyldihydroxy isobutyl-POSS.

Polysilsesquioxanes reinforcing agents of the present invention may be incorporated into known polymeric compositions, especially silicone-containing formulations useful in the manufacture of intraocular lenses. The method of incorporation can be different depending on the reactive groups of the POSS. Also, the polymer composition to be reinforced with POSSes should have functional groups reactive with one or more reactive groups of the POSS. For POSSes having Si—H or vinyl groups, the POSSes are incorporated into the polymeric composition through a hydrosilation reaction between the POSS and other components with Si-vinyl or Si—H groups in the formulation as set forth in Scheme 1 below. In Scheme 1 below, "silicone" means siloxane moieties in a formulation of interest, and the vinyl group can be an ethylenically unsaturated group such as vinyl, allyl, norbornenyl, fumarate, maleate, acrylate, methacrylate, acrylamide, methacrylamide or styrenyl. Also in Scheme 1 below, "R" represents a nonreactive connecting spacer between the Si atom and the reactive vinyl group.

Scheme 1

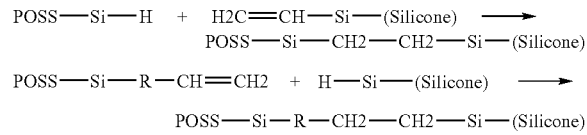

For POSSes having acrylic and/or styrene groups attached to Si, the polysilsesquioxanes are incorporated into the polymeric composition through a typical free radical copolymerization reaction.

For POSSes having alcohol, amine, thiol, epoxy and isocyanate groups attached to Si, the POSSes are incorporated into the polymeric composition through the typical epoxy or urethane resin reactions as set forth in Scheme 2 below wherein "silicone" means siloxane moieties in a formulation of interest, "Y" can be O, S or NH and "M" is an epoxy group or an isocyanate group.

Scheme 2

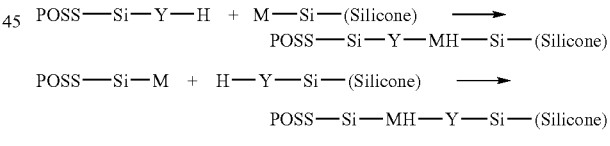

POSSes having acid or acid chloride groups can be incorporated into a formulation of interest through an ester/amide synthesis reaction with a molecule having OH, SH or NH groups.

Silicone containing formulations reinforced with the reactive POSSes of the present invention, including reactive polysiloxanes with reactive groups capable of reacting with the reactive groups of the POSSes of the present invention, may include for example but are not limited to polysiloxane-based prepolymers with polymerizable groups such as acrylate, methacrylate, acrylamide, methacrylamide, fumarate, maleate, norbornenyl and styrene groups, and polysiloxanes with multiple reactive groups such as hydrogen, hydroxy, alkoxy, amine, chlorine, epoxide, isocyanate, nitrile, vinyl and thiol groups. Some specific examples of such polysiloxanes include vinyl-terminated or methacrylate-terminated polydimethyl-co-diphenyl siloxanes and polydimethyl-co-methylhydro-siloxanes.

Durable IOLs having thin optic portions are critical in enabling a surgeon to minimize surgical incision size. Keeping the surgical incision size to a minimum reduces intraoperative trauma and postoperative complications. A thin IOL optic portion is also critical for accommodating certain anatomical locations in the eye such as the anterior chamber and the ciliary sulcus. IOLs may be placed in the anterior chamber for increasing visual acuity in both aphakic and phakic eyes and placed in the ciliary sulcus for increasing visual acuity in phakic eyes.

The polymeric compositions with reinforcing agents of the present invention have the durability and flexibility required to allow ophthalmic devices manufactured from the same to be folded or deformed for insertion into an eye through the smallest possible surgical incision, i.e., 3.0 mm or smaller.

One or more suitable ultraviolet light absorbers may optionally be added in the manufacture of the subject polymeric compositions with polysilsesquioxane reinforcing agents. Such ultraviolet light absorbers include for example but are not limited to β-(4-benzotriazoyl-3-hydroxyphenoxy) ethyl acrylate, 4-(2-acryloxyethoxy)-2-hydroxybenzophenone, 4-methacryloxy-2-hydroxybenzophenone, 2-(2'-methacryloxy-5'-methylphenyl)benzotriazole, 2-(2'-hydroxy-5'-methacryoxyethylphenyl)-2H-benzotriazole, 2-[3'-tert-butyl-2'-hydroxy-5'-(3"-methacryloyloxypropyl) phenyl]-5-chlorobenzotriazole, 2-[3'-tert-butyl-5'-(3"-dimethylvinylsilylpropoxy)-2'-hydroxyphenyl]-5-methoxybenzotriazole, 2-(3'-allyl-2'-hydroxy-5'-methylphenyl) benzotriazole, 2-[3'-tert-butyl-2'-hydroxy-5'-(3"-methacryloyloxypropoxy)phenyl]-5-methoxybenzotriazole, and 2-[3'-tert-butyl-2'-hydroxy-5'-(3"-methacryloyloxypropoxy)phenyl]-5-chlorobenzotriazole. The choice of ultraviolet light absorber depends on the level of UV blockage desired and the type of polymerizable groups present, i.e., the type of reaction, for curing to occur.

Soft, foldable, relatively high refractive index of approximately 1.45 or greater, relatively high elongation of approximately 100 percent or greater polymeric compositions of the present invention with one or more POSS reinforcing agents are described in still greater detail in the examples that follow.

EXAMPLE 1

Preparation of Polymeric Composition with Norbornenylethyl Isobutyl-POSS:

A glass vial is charged with 2.3 grams (2.45 milimole of vinyl) of norbornenylethyl isobutyl-POSS (Hybrid Plastics, Fountain Valley, Calif.) and 15 mL of tetrahydrofuran. The mixture was stirred until all POSS powder is dissolved. Then 0.7 grams (4.45 millimole of Si—H) of methylhydrosiloxane-dimethylsiloxane (50/50) of Mn around 1050 (Gelest Inc., Tullytown, Pa.) and 7.0 grams (0.254 millimole of vinyl) of vinyl-terminated diphenylsiloxane-dimthylsiloxane copolymer (15–17%) of Mn 55,000 (Gelest Inc., Tullytown, Pa.) are added and well mixed. The solvent is then removed under reduced pressure. Then 1.0 mg of Platinum (0)-cyclovinylmethysiloxane complex (Gelest Inc., Tullytown, Pa.) is added into the silicone mixture and mixed well prior to degassing. The mixture is then cast between two silane-treated glass plates and cured at 100° C. for two hours. The cured film is optically clear.

EXAMPLE 2

Preparation of Polymeric Composition with Trisnorbornenylethyl Isobutyl-POSS:

The procedure is the same as that of Example 1 except that 1.8 grams (4.07 milimole of vinyl) trisnorbornenylethyl-POSS (Hybrid Plastics, Fountain Valley, Calif.) is used to replace norbornenylethyl isobutyl-POSS and 1.2 gram (7.64 millimole of Si—H) methylhydrosiloxane-dimethylsiloxane (50/50) copolymer is used. The cured film is optically clear.

EXAMPLE 3

Preparation of Polymeric Composition with Tris(vinyldimethyl)Isobutyl-POSS:

The procedure is the same as that of Example 1 except that 1.8 grams (5.17 milimole of vinyl) of tris(vinyldimethyl)isobutyl-POSS (Hybrid Plastics, Fountain Valley, Calif.) is used rather than norbornenylethyl isobutyl-POSS and 1.2 gram (7.64 millimole of Si—H) methylhydrosiloxane-dimethylsiloxane (50/50) copolymer is used. The cured film is optically clear.

EXAMPLE 4

Preparation of Polymeric Composition with Methacryloxylpropyl-POSS:

The procedure is the same as that of Example 1 except that 1.2 grams (7.41 milimole of vinyl) of tris(vinyldimethyl)isobutyl-POSS (Hybrid Plastics, Fountain Valley, Calif.) is used to replace norbornenylethyl isobutyl-POSS and 1.8 gram (11.45 millimole of Si—H) of methylhydrosiloxane-dimethylsiloxane (50/50) copolymer is used. The cured film is optically clear.

EXAMPLE 5

Preparation of Polymeric Composition with Vinyl-POSS Cage Mixture:

The procedure is the same as that of Example 1 except that vinyl-POSS cage mixture (Hybrid Plastics, Fountain Valley, Calif.) in the amount of 1.1 grams (7.52 milimole of vinyl) is used to replace norbornenylethyl isobutyl-POSS and 1.9 gram (12.1 millimole of Si—H) of methylhydrosiloxane-dimethylsiloxane (50/50) copolymer is used. The cured film is optically clear.

Medical devices produced using the polymeric compositions with reinforcing agents of the present invention may be manufactured in accordance with methods known to those skilled in the art of the specific ophthalmic device being produced. For example, if an intraocular lens is to be produced, the same may be manufactured by methods known to those skilled in the art of intraocular lens production.

Ophthalmic devices such as but not limited to IOLs and cornea) inlays manufactured using the polymeric compositions with reinforcing agents of the present invention can be of any design capable of being rolled or folded for implantation through a relatively small surgical incision, i.e., 3.0 mm or less. For example, intraocular implants such as IOLs comprise an optic portion and one or more haptic portions. The optic portion reflects light onto the retina and the permanently attached haptic portions hold the optic portion in proper alignment within an eye. The haptic portions may be integrally formed with the optic portion in a one-piece design or attached by staking, adhesives or other methods known to those skilled in the art in a multipiece design.

The subject ophthalmic devices, such as for example IOLs, may be manufactured to have an optic portion and haptic portions made of the same or differing materials. Preferably, in accordance with the present invention, both the optic portion and the haptic portions of the IOLs are made of the same polymeric composition with one or more reinforcing agents of the present invention. Alternatively however, the IOL optic portion and haptic portions may be manufactured from different materials and/or different formulations of the polymeric compositions with one or more reinforcing agents of the present invention, such as described in detail in U.S. Pat. Nos. 5,217,491 and 5,326,506, each incorporated herein in their entirety by reference. Once the material(s) are selected, the same may be cast in molds of the desired shape or cast in the form of rods and lathed or machined into disks. If cast in the form of rods and lathed or machined into disks, the disks may then be lathed or machined at a relatively low temperature below that of the glass transition temperature of the material(s) to produce IOLs. The IOLs whether molded or machined are then cleaned, polished, packaged and sterilized by customary methods known to those skilled in the art.

In addition to IOLs, the polymeric compositions with one or more reinforcing agents of the present invention are also suitable for use in the production of other ophthalmic devices such as contact lenses, keratoprostheses, capsular bag extension rings, corneal inlays, corneal rings and like devices.

Ophthalmic devices manufactured using the unique polymeric compositions with one or more reinforcing agents of the present invention are used as customary in the field of ophthalmology. For example, in a surgical cataract procedure, an incision is placed in the cornea of an eye. Through the corneal incision the cataractous natural lens of the eye is removed (aphakic application) and an IOL is inserted into the anterior chamber, posterior chamber or lens capsule of the eye prior to closing the incision. However, the subject ophthalmic devices may likewise be used in accordance with other surgical procedures known to those skilled in the field of ophthalmology.

While shown and described herein certain reinforcing agents, polymeric compositions with one or more reinforcing agents, methods of producing the reinforcing agents and polymeric compositions with one or more reinforcing agents and ophthalmic devices made from the subject polymeric compositions with one or more reinforcing agents in accordance with the present invention, it will be manifest to those skilled in the art that various modifications may be made without departing from the spirit and scope of the underlying inventive concept and that the same is not limited to particular structures herein shown and described except insofar as indicated by the scope of the appended claims.

We claim:

1. A polymeric material comprising a reaction product of:
   (a) a polyhedral oligomeric silsesquioxane ("POSS") having a formula of

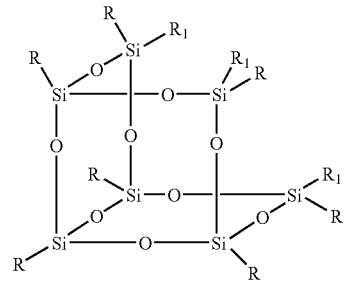

wherein the R1 groups are the same or different reactive groups selected from the group consisting of hydrogen, hydroxy, alkoxy, amine, chlorine, epoxide, isocyanate, methacrylate, acrylate, methacrylamide, acylamide, nitrile, norbornenyl, vinyl, styrenyl and thiol, with or without a spacer selected from the group consisting of hydrocarbon groups, silyl groups, and siloxy groups; and the R groups may be the same or different selected from the group consisting of $C_{1-30}$ alkyl and $C_{6-30}$ aryl; and (b) a polymeric composition having other reactive groups that are capable of reacting with the reactive $R_1$ groups to form the polymeric material;

wherein the polymeric material further has properties compatible with an ophthalmic environment.

2. The polymeric material of claim 1, wherein at least one of said $R_1$ groups is a vinyl group.

3. The polymeric material of claim 1, wherein at least one of said $R_1$ groups is a hydrogen group.

4. The polymeric material of claim 1, wherein at least one of said $R_1$ groups is a hydroxy group.

5. The polymeric material of claim 1, wherein at least one of said $R_1$ groups is an amine group.

6. A flexible ophthalmic device reinforcing composition comprising

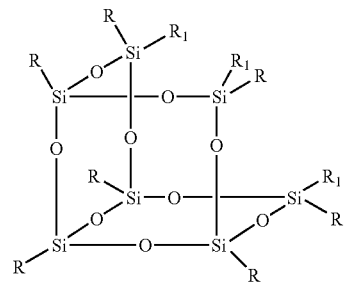

wherein the $R_1$ groups are the same or different reactive groups selected from the group consisting of hydrogen, epoxide, methacrylate, acrylate, methacrylamide, acrylamide, nitrile. norbornenyl, vinyl, styrenyl and thiol, with or without a spacer selected from the group consisting of hydrocarbon groups, silyl groups, and siloxy groups; the R groups may be the same or different selected from the group consisting of $C_{1-30}$ alkyl and $C_{6-30}$ aryl; and the composition is useful as a reinforcing agent in the manufacture of flexible ophthalmic implants.

7. A flexible ophthalmic device reinforcing composition comprising

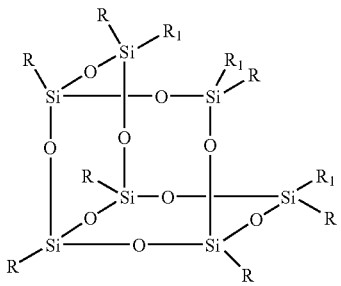

wherein the $R_1$ groups are the same or different reactive groups selected from the group consisting of hydrogen, epoxide, methacrylate, acrylate, methacrylamide, acrylamide, nitrile, norbornenyl, vinyl, styrenyl and thiol, with or without a spacer selected from the group consisting of hydrocarbon groups, silyl groups, and siloxy groups; the R groups may be the same or different selected from the group consisting of ethyl, butyl, isooctyl, cyclopentyl, cyclohexyl, and phenyl and the composition is useful as a reinforcing agent in the manufacture of flexible ophthalmic implants.

8. The polymeric material of claim 1, wherein at least one of said $R_1$ groups is a styrenyl group.

9. The polymeric material of claim 1, wherein at least one of said $R_1$ groups is an epoxide group or a nitrile group.

10. The polymeric material of claim 1, wherein at least one of said $R_1$ groups is a norbornenyl group.

11. The polymeric material of claim 1, wherein said POSS further comprising an acid group.

12. The polymeric material of claim 1, wherein at least one of said $R_1$ groups is a methacrylate group, an acrylate group, a methacrylamide group or an acrylamide group.

13. The polymeric material of claim 1, wherein at least one of said R groups is an aryl group.

14. The polymeric material of claim 1, wherein at least one of said $R_1$ groups is a chlorosilane group.

15. A method of producing a polymeric material, said method comprising:
(a) providing a POSS having a T7 structure or a T8 structure, said POSS having at least one reactive group selected from the group consisting methacrylate, acrylate, methacrylamide, acrylamide, and norbornenyl, with or without a spacer selected from the group consisting of hydrocarbon groups, silyl groups, and siloxy groups;
(b) providing a polymeric composition having other reactive groups that are capable of reacting with said at least one reactive group of said POSS; and
(c) reacting said POSS with said polymeric composition to form said polymeric material;
wherein said reacting is effected by a hydrosilation reaction.

16. A method of producing a polymeric material the method comprising:
(a) providing a POSS having a T7 structure, said POSS having at least one reactive group selected from the group consisting of hydrogen, hydroxy, alkoxy, amine, chlorine, epoxide, isocyanate, methacrylate, acrylate, methacrylamide, acrylamide, nitrile, norbornenyl, vinyl, styrenyl and thiol, with or without a spacer selected from the group consisting of hydrocarbon groups, silyl groups, and siloxy groups;
(b) providing a polymeric composition having other reactive groups that are capable of reacting with said at least one reactive group of said POSS; and
(c) reacting said POSS with said polymeric composition to form said polymeric material;
wherein said reacting is effected by a free radical copolymerization reaction.

17. A method of producing a polymeric material, the method comprising:
(a) providing a POSS having a T7 structure, said POSS having at least one reactive group selected from the group consisting of hydroxy, alkoxy, amine, epoxide, isocyanate, nitrile, and thiol, with or without a spacer selected from the group consisting of hydrocarbon groups, silyl groups, and siloxy groups;
(b) providing a polymeric composition having other reactive groups that are capable of reacting with said at least one reactive group of said POSS; and
(c) reacting said POSS with said polymeric composition to form said polymeric material;
wherein said reacting is effected by an ester/amide synthesis reaction.

18. A method of producing an ophthalmic device comprising:
(a) casting a polymeric material in the form of a rod, the polymeric material comprising a reaction product of:
(1) a polyhedral oligomeric silsesquioxane ("POSS") having a formula of

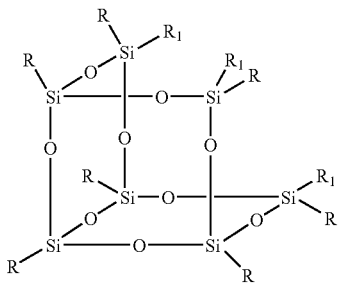

wherein the $R_1$ groups are the same or different reactive groups selected from the group consisting of hydrogen, hydroxy, alkoxy, amine, chlorine, epoxide, isocyanate, methacrylate, acrylate, methacrylamide, acrylamide, nitrite, Norbornenyl, vinyl, styrenyl and thiol, with or without a spacer selected from the group consisting of hydrocarbon groups, silyl groups, and siloxy groups; and the R groups may be the same or different selected from the group consisting of $C_{1-30}$ alkyl and $C_{6-30}$ aryl; and
(2) a polymeric composition having other reactive groups that are capable of reading with the reactive $R_1$ groups to form the polymeric material;
wherein the polymeric material further has properties compatible with an ophthalmic environment
(b) lathing or machining said rod into disks; and
(c) lathing or machining said disks Into the ophthalmic device.

19. A method of producing an ophthalmic device comprising:
(a) pouring a polymeric material prior to curing into a mold, the polymeric material comprising a reaction product of:
(1) a polyhedral oligomeric silsesquioxane ("POSS") having a formula of

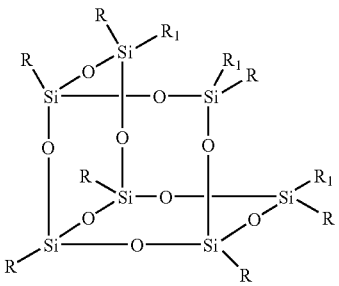

wherein the $R_1$ groups are the same or different reactive groups selected from the group consisting of hydrogen, hydroxy, alkoxy, amine, chlorine, epoxide, isocyanate, methacrylate, acrylate, methacrylamide, acrylamide, nitrile, norbornenyl, vinyl, styrenyl and thiol, with or without a spacer selected from the group consisting of hydrocarbon groups, silyl groups, and siloxy groups; and the R groups may be the same or different selected from the group consisting of $C_{1-30}$ alkyl and $C_{6-30}$ aryl; and (2) a polymeric composition having other reactive groups that are capable of reacting with the reactive $R_1$ groups to form the polymeric material;

wherein the polymeric material further has properties compatible with an ophthalmic environment;

(b) curing said polymeric material to form the ophthalmic device; and (c) removing said ophthalmic device from said mold following curing thereof.

20. The polymeric material of claim 1, wherein said POSS is trisnorbornenylethyl isobutyl-POSS.

21. The polymeric material of claim 1, wherein said POSS is trisnorbornenylethyl isooctyl-POSS.

22. The polymeric material of claim 1, wherein at least one of said $R_1$ groups is an alkoxy group.

23. The polymeric material of claim 1, wherein at least one of said $R_1$ groups is an isocyanate group.

24. A polymeric material comprising a reaction product of:

(a) a POSS having a T7 structure, said POSS having at least one reactive group selected from the group consisting of hydrogen, hydroxy, alkoxy, amine, chlorine, epoxide, isocyanate, methacrylate, acrylate, methacrylamide, acrylamide, nitrile, norbornenyl, vinyl, styrenyl and thiol, with or without a spacer selected from the group consisting of hydrocarbon groups, silyl groups, and siloxy groups; and (b) a polymeric composition having other reactive groups that are capable of reacting with said at least one reactive group of said POSS to form the polymeric material.

25. A method of producing a polymeric material, said method comprising:

(a) providing a POSS having a T7 structure, said POSS having at least one reactive group selected from the group consisting of hydroxy, alkoxy, amine, chlorine, epoxide, isocyanate, methacrylate, acrylate, methacrylamide, acrylamide, nitrite, norbornenyl, vinyl, styrenyl, and thiol, with or without a spacer selected from the group consisting of hydrocarbon groups, silyl groups, and siloxy groups;

(b) providing a polymeric composition having other reactive groups that are capable of reacting with said at least one reactive group of said POSS; and (c) reacting said POSS with said polymeric composition to form said polymeric material.

26. A method of producing a polymeric material, said method comprising:

(a) providing a POSS having a formula of

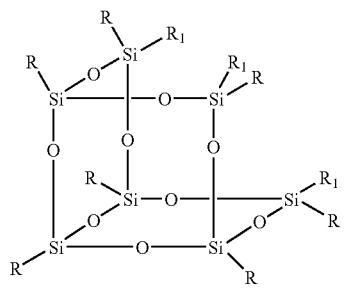

wherein the $R_1$ groups are the same or different reactive groups selected from the group consisting of hydrogen, hydroxy, alkoxy, amine, chlorine, epoxide, isocyanate, methacrylate, acrylate, methacrylamide, acrylamide, nitrile, norbornenyl, vinyl, styrenyl and thiol, with or without a spacer selected from the group consisting of hydrocarbon groups, silyl groups, and siloxy groups; and the R groups may be the same or different selected from the group consisting of $C_{1-30}$ alkyl and $C_{6-30}$ aryl; and (b) providing a polymeric composition having other reactive groups that are capable of reacting with the reactive $R_1$ groups; and (c) reacting the POSS with the polymeric composition to form the polymeric material:

wherein the POSS and the polymeric composition are chosen such that the polymeric material further has properties compatible with an ophthalmic environment.

27. An ophthalmic device comprising a polymeric material that comprises a reaction product of:

(a) a PC)SS having a T7 structure or a T8 structure said POSS having at least one reactive group selected from the group consisting of hydroxy, alkoxy, amine, chlorine, epoxide, isocyanate, methacrylate, acrylate, methacrylamide, acrylamide, nitrile, norbornenyl, and thiol, with or without a spacer selected from the group consisting of hydrocarbon groups, silyl groups, and siloxy groups; and (b) a polymeric composition having other reactive groups that are capable of reacting with said at least one reactive group of said POSS to form the polymeric material.

28. An ophthalmic device comprising a polymeric material that comprises a reaction product of:

(a) a POSS having a formula of

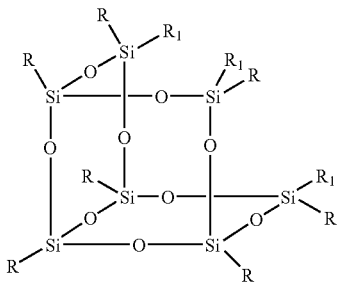

wherein the $R_1$ groups are the same or different reactive groups selected from the group consisting of hydrogen, hydroxy, alkoxy, amine, chlorine, epoxide, isocyanate, methacrylate, acrylate, methacrylamide, acrylamide, nitrile, norbornenyl, vinyl, styrenyl and thiol, with or without a spacer selected from the group consisting of hydrocarbon groups, silyl groups, and siloxy groups; and the R groups may be the same or different selected from the group consisting of $C_{1-30}$ alkyl and $C_{6-30}$ aryl; and (b) a polymeric composition having other reactive groups that are capable of reacting with the reactive $R_1$ groups;

wherein the polymeric material further has properties compatible with an ophthalmic environment.

29. A method of producing a polymeric material the method comprising;
  (a) providing a POSS having a T8 structure, said POSS having at least one reactive group selected from the group consisting of alkoxy, methacrylamide, acrylamide, and thiol, with or without a spacer selected from the group consisting of hydrocarbon groups, silyl groups, and siloxy groups;
  (b) providing a polymeric composition having other reactive groups that are capable of reading with said at least one reactive group of said POSS; and
  (c) reacting said POSS with said polymeric composition to form said polymeric material;

wherein said reacting is effected by a free radical copolymerization reaction.

* * * * *